(12) United States Patent
Cho

(10) Patent No.: US 9,585,996 B2
(45) Date of Patent: Mar. 7, 2017

(54) BLOOD PURIFYING FILTER AND BLOOD PURIFYING APPARATUS

(71) Applicant: Taebeom Cho, Daejeon (KR)

(72) Inventor: Taebeom Cho, Daejeon (KR)

(73) Assignee: HUMAN BIOMED, INC.VT (US)

( * ) Notice: Subject to any disclaimer, the term of this patent is extended or adjusted under 35 U.S.C. 154(b) by 0 days.

(21) Appl. No.: 14/811,776

(22) Filed: Jul. 28, 2015

(65) Prior Publication Data

US 2016/0074570 A1 Mar. 17, 2016

Related U.S. Application Data

(63) Continuation-in-part of application No. 14/243,137, filed on Apr. 2, 2014.

(30) Foreign Application Priority Data

Jul. 28, 2014 (KR) ........................ 10-2014-0095603

(51) Int. Cl.
*A61M 1/34* (2006.01)
*A61M 1/36* (2006.01)
(Continued)

(52) U.S. Cl.
CPC ............ *A61M 1/3479* (2014.02); *A61M 1/16* (2013.01); *A61M 1/3417* (2014.02); *A61M 1/3472* (2013.01); *A61M 1/3486* (2014.02); *A61M 1/3496* (2013.01); *A61M 1/3679* (2013.01); *B01D 61/58* (2013.01); *B01D 63/04* (2013.01);
(Continued)

(58) Field of Classification Search
CPC .............. A61M 1/3472; A61M 1/3486; A61M 1/3679; A61M 1/3496; A61M 1/3417; A61M 1/3479; A61M 1/16; A61M 2205/75; B01D 61/243; B01D 61/58; B01D 63/04; B01D 2311/2626; B01D 2311/2649; B01D 2313/08; B01D 2313/10; B01D 2313/12; B01D 2313/20; B01D 2313/21; B01D 2313/40; B01D 2319/00; B01D 2319/02;
(Continued)

(56) References Cited

U.S. PATENT DOCUMENTS 6,270,674 B1* 8/2001 Baurmeister .......... B01D 15/08
210/321.79
7,285,106 B2* 10/2007 Collins ................ B01D 61/142
210/321.64
(Continued)

FOREIGN PATENT DOCUMENTS

KR 10-2006-0057176 5/2006
KR 10-2009-0027173 3/2009
KR 10-2014-0077804 6/2014

*Primary Examiner* — John Kim
(74) *Attorney, Agent, or Firm* — Lee Global Patent, LLC

(57) ABSTRACT

Provided are a blood purifying filter and a blood purifying apparatus having the same. The blood purifying filter includes a plasma separation filter separating plasma from blood, a hemodialysis filter configured in parallel with the plasma separation filter to remove toxins and waste products from blood, a housing providing installation space for the plasma separation filter and the hemodialysis filter, and plasma inlet and outlet ports provided in the housing. The housing further includes a wall, a lower cap and an upper cap which are coupled to the plasma separation filter and the hemodialysis filter.

13 Claims, 17 Drawing Sheets

(51) Int. Cl.
*B01D 61/24* (2006.01)
*B01D 61/58* (2006.01)
*B01D 63/04* (2006.01)
*A61M 1/16* (2006.01)
*B01J 20/28* (2006.01)

(52) U.S. Cl.
CPC ........ B01D 63/043 (2013.01); B01J 20/2805 (2013.01); *A61M 2205/75* (2013.01); *B01D 61/243* (2013.01); *B01D 2311/2626* (2013.01); *B01D 2311/2649* (2013.01); *B01D 2313/08* (2013.01); *B01D 2313/20* (2013.01); *B01D 2313/21* (2013.01); *B01D 2313/40* (2013.01); *B01D 2319/02* (2013.01); *B01D 2319/04* (2013.01)

(58) Field of Classification Search
CPC ............... B01D 2319/04; B01D 63/043; B01J 20/2805
See application file for complete search history.

(56) References Cited

U.S. PATENT DOCUMENTS

| | | | |
|---|---|---|---|
| 2010/0282662 A1* | 11/2010 | Lee | A61M 1/3472 210/266 |
| 2012/0063954 A1* | 3/2012 | Passlick-Deetjen | A61M 1/3679 422/44 |
| 2015/0273127 A1* | 10/2015 | Flieg | A61M 1/3679 210/266 |

* cited by examiner

FIG. 7
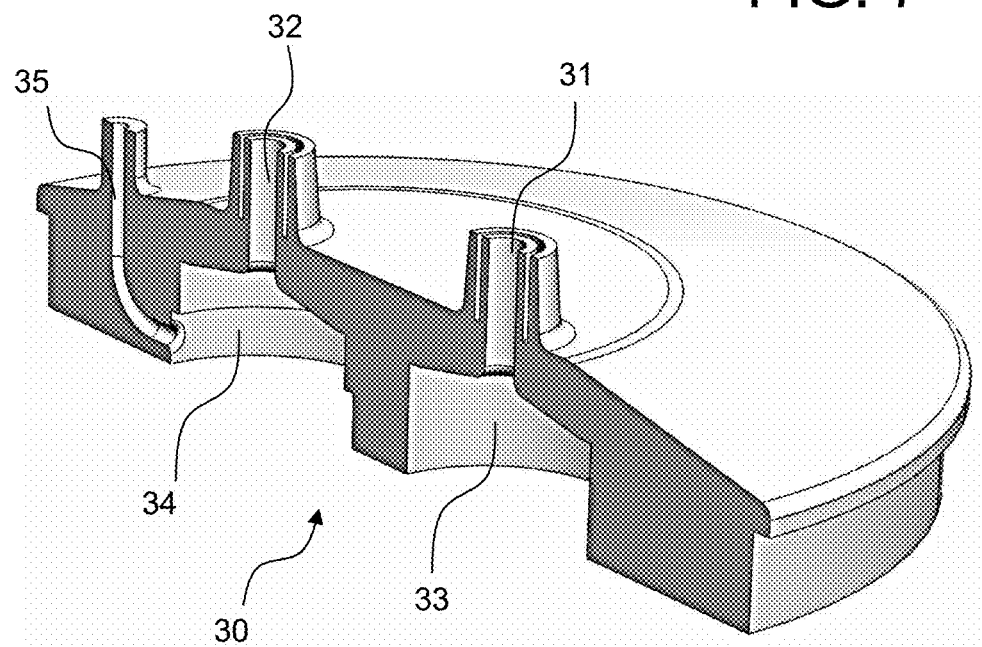
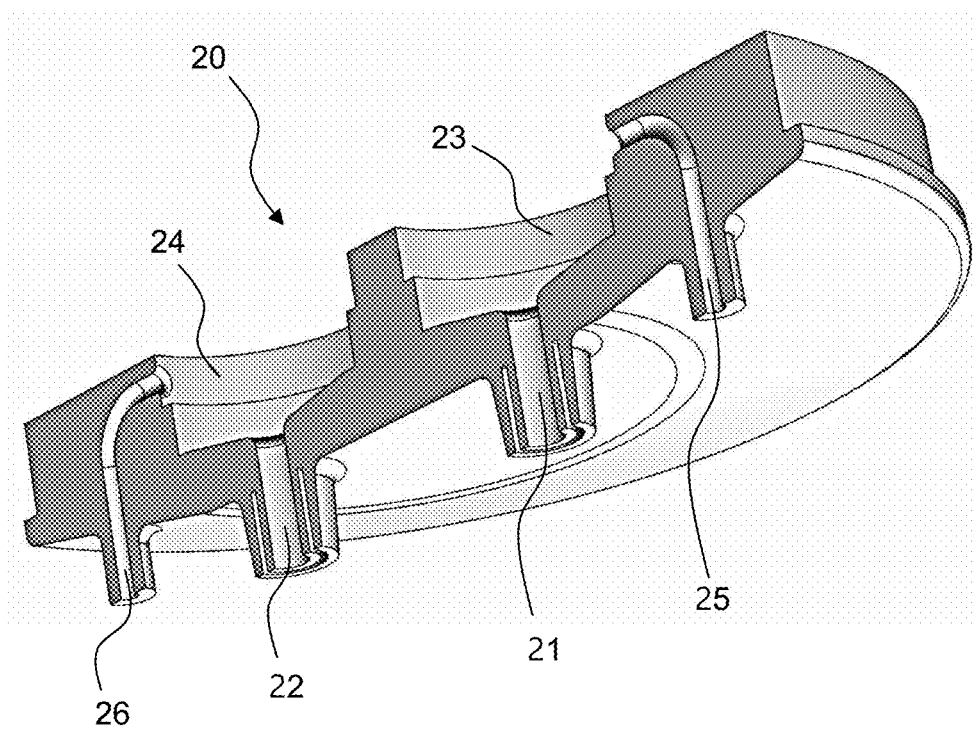

FIG. 8
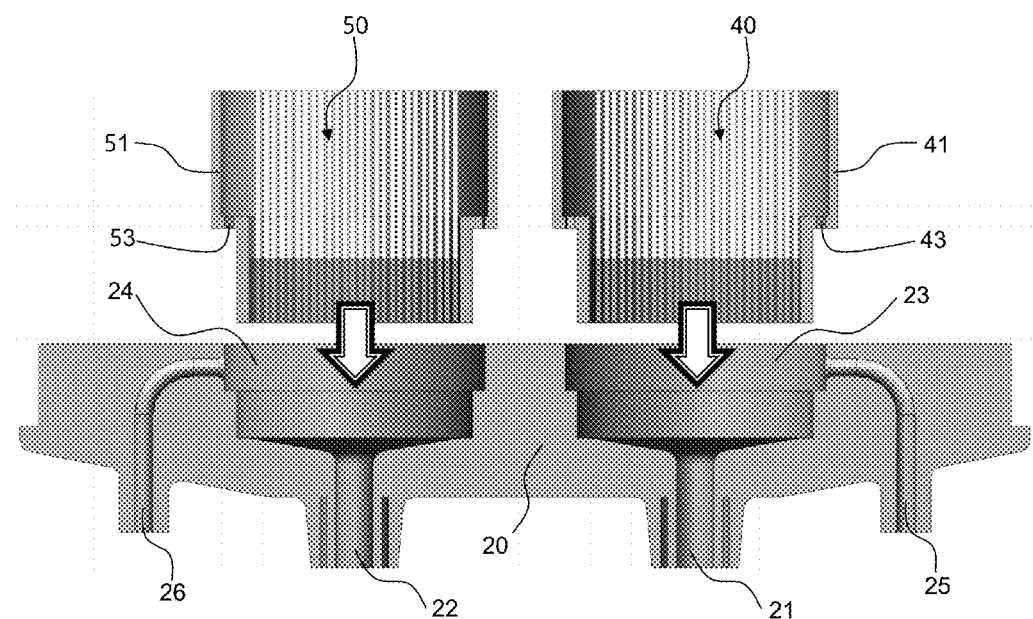
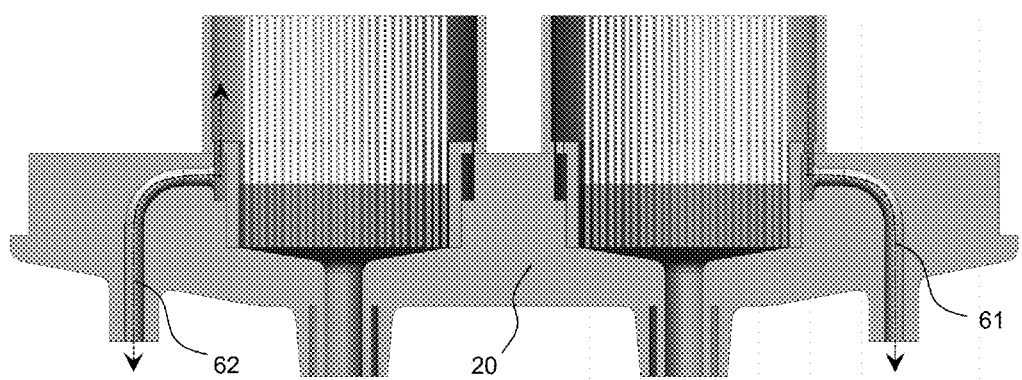

FIG. 9
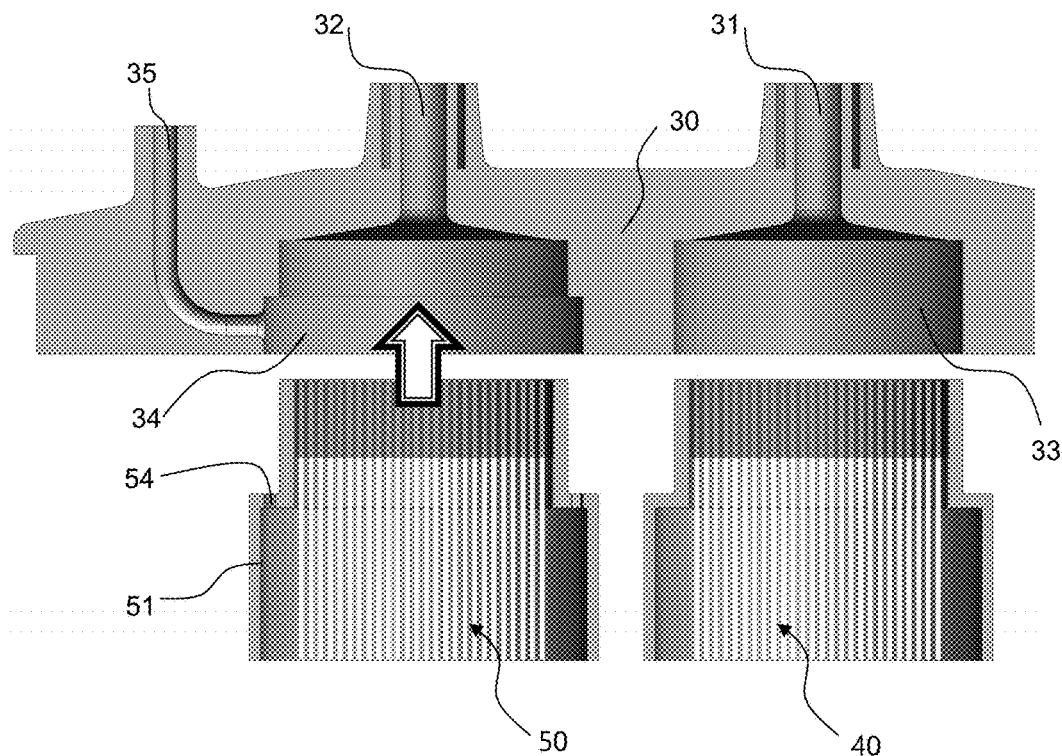
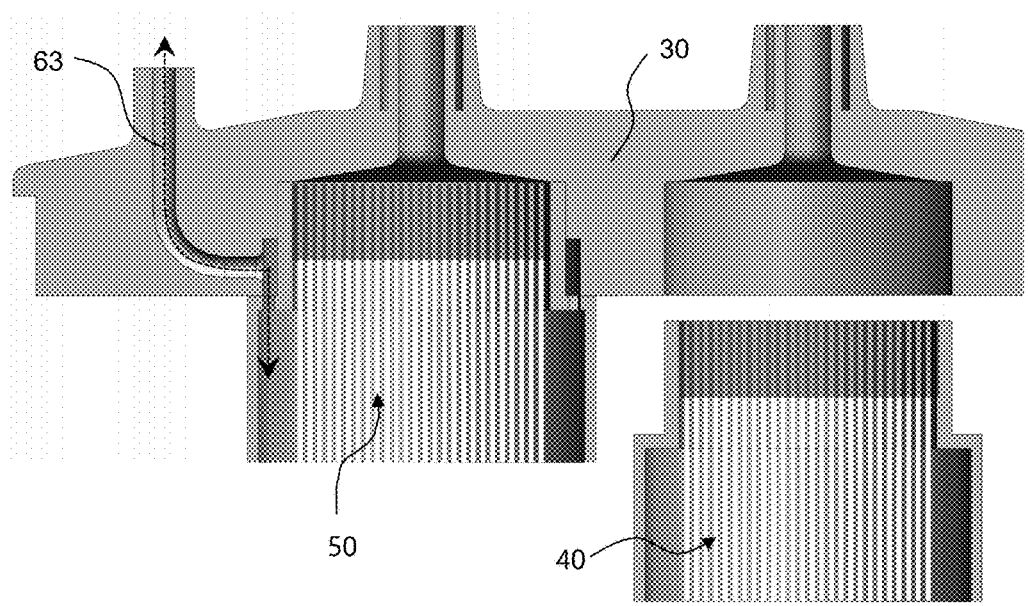

BLOOD PURIFYING FILTER AND BLOOD PURIFYING APPARATUS

CROSS-REFERENCE TO RELATED APPLICATIONS

Pursuant to 35 U.S.C. §119, this application claims the benefit of priority to Korean Patent Application No. 10-2014-0095603, filed Jul. 28, 2014 in the Korean Intellectual Property Office, and this application is a continuation-in-part of U.S. patent application Ser. No. 14/243,137 filed Apr. 2, 2014, entitled BLOOD PURIFYING FILTER AND BLOOD PURIFYING APPARATUS HAVING THE SAME, the entire contents of which are hereby incorporated by reference in their entirety.

BACKGROUND

The present invention relates to a blood purifying filter and a blood purifying apparatus including the blood purifying filter, which are configured to separate plasma from blood of a patient using a plasma separation filter, remove hepatic toxins from the separated plasma using adsorbents, such as activated charcoal or anion exchange resin, and simultaneously perform hemodialysis which removes water-soluble toxins and uremic toxins from blood.

When a liver function is damaged, the toxins and waste products to be removed from a body by the liver are accumulated in the body. If the liver transplant is not performed in a timely manner, the blood purification treatment such as dialysis, filtration or adsorption in which blood is circulated out of body must be performed to remove those toxic substances.

Liver performs many functions such as a metabolic function of treating various nutrients existing in our body, a function to store nutrients required by our body, a synthesizing function to synthesize gall juice and albumin, and a function to detoxify various toxins brought into our body such as alcohol or drug. Accordingly, when a liver is damaged, the substances such as ammonia and bilirubin to be removed from a body by the hepatic metabolism are accumulated in the body. The accumulation causes complications such as jaundice, hepatic encephalopathy, and multiple organ failure.

In case of acute liver failure, a liver transplant is regarded as the decisive cure. However, as shown by the liver transplant data published by OPTN/SRTR Annual Report in 2011, only 36% of the patients waiting for the liver transplant actually receive the treatment. In addition, according to the organ transplantation report from Korean Network for Organ Sharing (KONOS), only 22% of the patients on the waiting list receive the liver transplant. It is because the donor organs are substantially short as compared with the required numbers of liver transplant. Therefore, an artificial liver treatment is required for liver failure patients to serve the function until a liver transplant or self-recovery.

Artificial liver apparatuses currently in clinical use are limited to MARS of Gambro Inc and Prometheus of FMC. MARS removes hepatic toxins from blood by adding a plasma protein called albumin in dialysis fluid. Since albumin is expensive, MARS comes to a costly treatment. Prometheus has such configuration that plasma is separated from blood to be filtered through ion-exchange resin adsorbent for removal of toxins existing in the plasma and then hemodialysis is performed after the plasma separation and adsorption. Accordingly, Prometheus apparatus has a complicated system including a plasma separation filter, two adsorption filters, and hemodialysis process, giving rise to a high treatment cost like MARS.

In order to solve such limitations of typical artificial liver systems, Korean Patent No. 1071402 entitled "Apparatus for Purifying Blood" discloses an apparatus that is configured to remove toxins from plasma without using expensive albumin and integrate plasma separation and absorption processes into a single filter. By implementing plasma separation and adsorption processes in a single filter, the entire artificial liver system is simplified from the typical artificial liver apparatuses. However, the system still requires additional hemofiltration or hemodialysis process. That is, in a case of a patient who needs intensive blood purifying treatment for liver failure, the removal of water-soluble toxins by hemodialysis or hemofiltration is as important as the removal of liver toxins or protein-bound toxins through adsorption.

As a method of overcoming such limitations, an apparatus which further simplifies the blood purification system by implementing plasma separation, plasma adsorption and hemodialysis in a single filter is also disclosed in Korean Patent Publication No. 2014-0077804. The plasma is separated across the plasma separation membrane by the operation of plasma pump, and the separated plasma passes through a plasma flow hole and a plasma flow section which is filled with adsorbents. In other words, plasma is configured to pass through the plasma separation membrane, the plasma flow hole and the plasma flow section filled with adsorbents, all of which act as resistance to plasma flow. Accordingly, despite the operation of the plasma pump, it is substantially limited to attain plasma flow rates required for the treatment.

SUMMARY OF THE DISCLOSURE

The present invention provides a blood purifying filter and an apparatus having the blood purifying filter, which efficiently purifies blood of a patient, enables simplification and miniaturization of the whole blood purifying apparatus, and provides convenience in installation and use, by integrating a plasma separation process for separating plasma from blood, an adsorption process for removing toxins from the separated plasma, and a hemodialysis process for removing uremic toxins from blood by a single filter.

Embodiments of the present invention provide blood purifying filters including: a plasma separation filter separating plasma from blood; a hemodialysis filter in parallel with the plasma separation filter removing toxins and waste products from blood; a housing providing installation spaces for the plasma separation filter and the hemodialysis filter and defining a plasma flow section outside the plasma separation filter and the hemodialysis filter; a plasma inlet port provided at one side of the housing to allow plasma to flow into the plasma flow section; and a plasma outlet port provided at one side of the housing to allow plasma passing the plasma flow section to be discharged out of the blood purifying filter. The housing may include a wall having a cylindrical shape, a lower cap coupled to the plasma separation filter and the hemodialysis filter at a lower side of the wall, and an upper cap coupled to the plasma separation filter and the hemodialysis filter at an upper side of the wall.

The plasma separation filter and the hemodialysis filter may include a housing having an internal space thereof and a membrane disposed in the internal space of the housing. The internal space of the housing is divided by the membrane to allow two fluids to flow.

The lower cap may be provided with a first lower-cap blood port connected to the plasma separation filter, a second lower-cap blood port connected to the hemodialysis filter, a first lower-cap insertion groove to be easily coupled to the plasma separation filter, and a second lower-cap insertion groove to be easily coupled to the hemodialysis filter. Similarly, the upper cap may be provided with a first upper-cap blood port connected to the plasma separation filter, a second upper-cap blood port connected to the hemodialysis filter, a first upper-cap insertion groove to be easily coupled to the plasma separation filter, and a second upper-cap insertion groove to be easily coupled to the hemodialysis filter.

The plasma separation filter housing may have a first flow hole in a side thereof where the plasma separation filter housing is coupled to the first lower-cap insertion groove. Also, the lower cap may be additionally provided with a first lower-cap passage, which penetrates the lower cap, with one end connected to the first lower-cap insertion groove. In this instance, the plasma separation filter is coupled to the lower cap, allowing the first flow hole provided in the plasma separation filter housing and the first lower-cap passage provided in the lower cap to be connected to each other and thus forming a first flow path 61. Plasma of the plasma separation filter flows through the first flow path.

In the same manner, the hemodialysis filter housing may have a second flow hole in the side thereof where the hemodialysis filter housing is coupled to the second lower-cap insertion groove, and the lower cap may be additionally provided with a second lower-cap passage, which penetrates the lower cap, having one end connected to the second lower-cap insertion groove. When the hemodialysis filter is coupled to the lower cap, the second flow hole and the second lower-cap passage are connected to each other and thus form a second flow path. Dialysate can be supplied or discharged through the second flow path.

Furthermore, the hemodialysis filter housing may also have a third flow hole in a side where the hemodialysis filter housing is coupled to the second upper-cap insertion groove, and the upper cap may be provided with an upper-cap passage which penetrates the upper cap and is connected the second upper-cap insertion groove. When the hemodialysis filter and the upper cap are coupled to each other, a third flow path connecting the third flow hole and the upper-cap passage may be formed. Dialysate can be supplied to the hemodialysis filter through one of the second and third flow paths and then discharged through the other one.

The blood purifying filter according to an embodiment of the present invention may further include a plasma connection tube which connects the lower cap and the plasma inlet port. Plasma of the plasma separation filter is discharged out of the plasma separation filter through the first lower-cap passage and then supplied to the plasma flow section through the plasma connection tube.

In addition, an adsorbent may be provided in the plasma flow section to remove toxins and waste products from plasma. The adsorbent included in the blood purifying filter according to an embodiment of the present invention is not limited in the type and number, and may be modified according to the purpose of the blood purifying treatment. Also, the adsorbent must not move through the plasma inlet and outlet ports.

The blood purifying apparatus according to an embodiment of the present invention may include the blood purifying filter, a blood flow tube connecting a patient and the blood purifying filter and allowing blood to flow therein, a blood pump disposed on the blood flow tube to transfer blood, a plasma pump disposed on the plasma connection tube to transfer plasma, a plasma flow tube connecting the plasma outlet port and the blood flow tube to allow plasma to flow therein, and a dialysate supply device supplying dialysate into the hemodialysis filter and collecting dialysate or filtrate from the hemodialysis filter. An additional plasma pump may be provided on the plasma flow tube. In addition, the hemodialysis filter can be easily switched into a function of hemofiltration in which excess water and waste products in blood are removed by the fluid pulling due to the dialysate supply device without the supply and discharge of dialysate by the dialysate supply device.

In the blood purifying apparatus according to an embodiment of the present invention, the hydraulic pressure of plasma flowing into the plasma flow section may be positive (+) value which is higher than the atmosphere pressure because of the operation of the plasma pump disposed on the plasma connection tube. The blood purifying filter according to an embodiment of the present invention is provided with the first flow path connecting the first flow hole and the first lower-cap passage and the plasma connection tube connecting the first flow path and the plasma inlet port. Accordingly, plasma passing through the plasma connection tube and the plasma flow section can be transferred by the fluid pushing of the plasma pump disposed on the plasma connection tube, such that the pressure of plasma flowing into the plasma flow section can be maintained positive (+) values. Positive plasma pressures can prevent problems such as an air inflow or the reduction in the plasma flow rate and toxin removal efficiency.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 7 is a perspective view of a lower cap and an upper cap;

FIG. 8 is a cross-sectional view illustrating a combination structure of a plasma separation filter, a hemodialysis filter, and a lower cap;

FIG. 9 is a cross-sectional view illustrating a combination structure of a plasma separation filter, a hemodialysis filter, and an upper cap;

DETAILED DESCRIPTION OF PREFERRED EMBODIMENTS

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

Hereinafter, a blood purifying filter according to an embodiment of the present invention will be described in detail with reference to the accompanying drawings.

Figure 1:
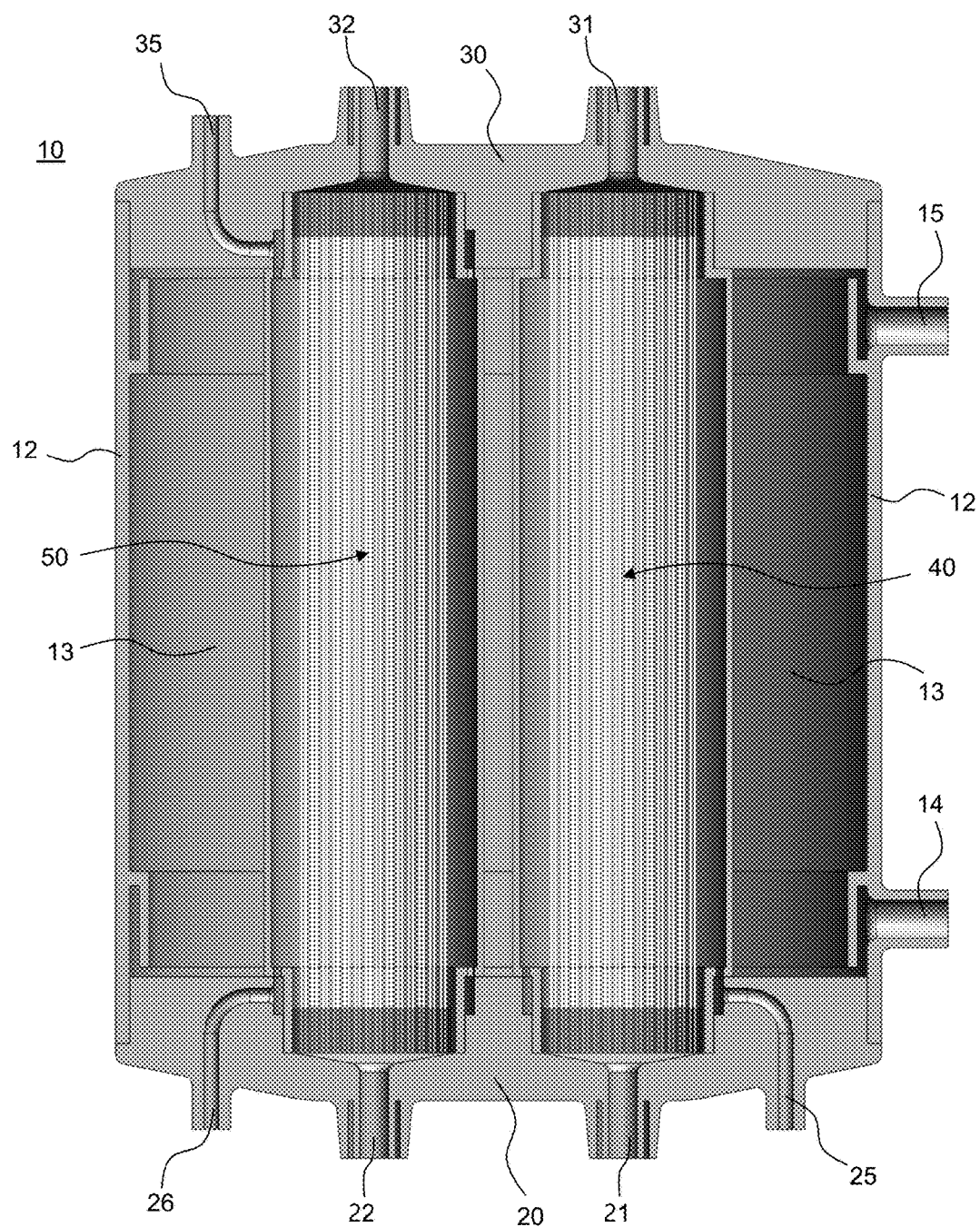
FIGS. 1 to 3 are a cross-sectional view, an exploded cross-sectional view and a perspective view illustrating an internal configuration of a blood purifying filter according to an embodiment of the present invention.
Figure 2:
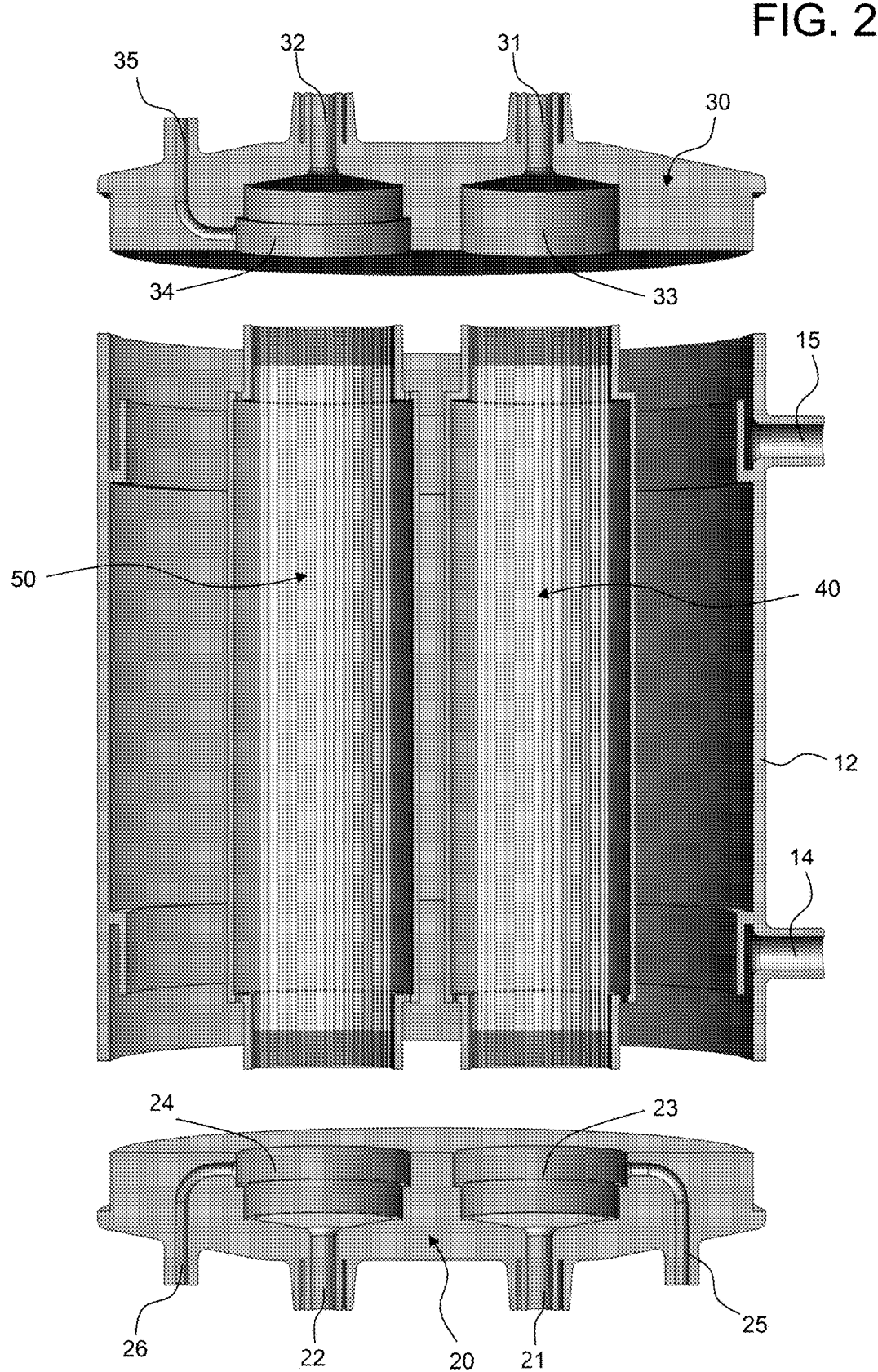
Figure 3:
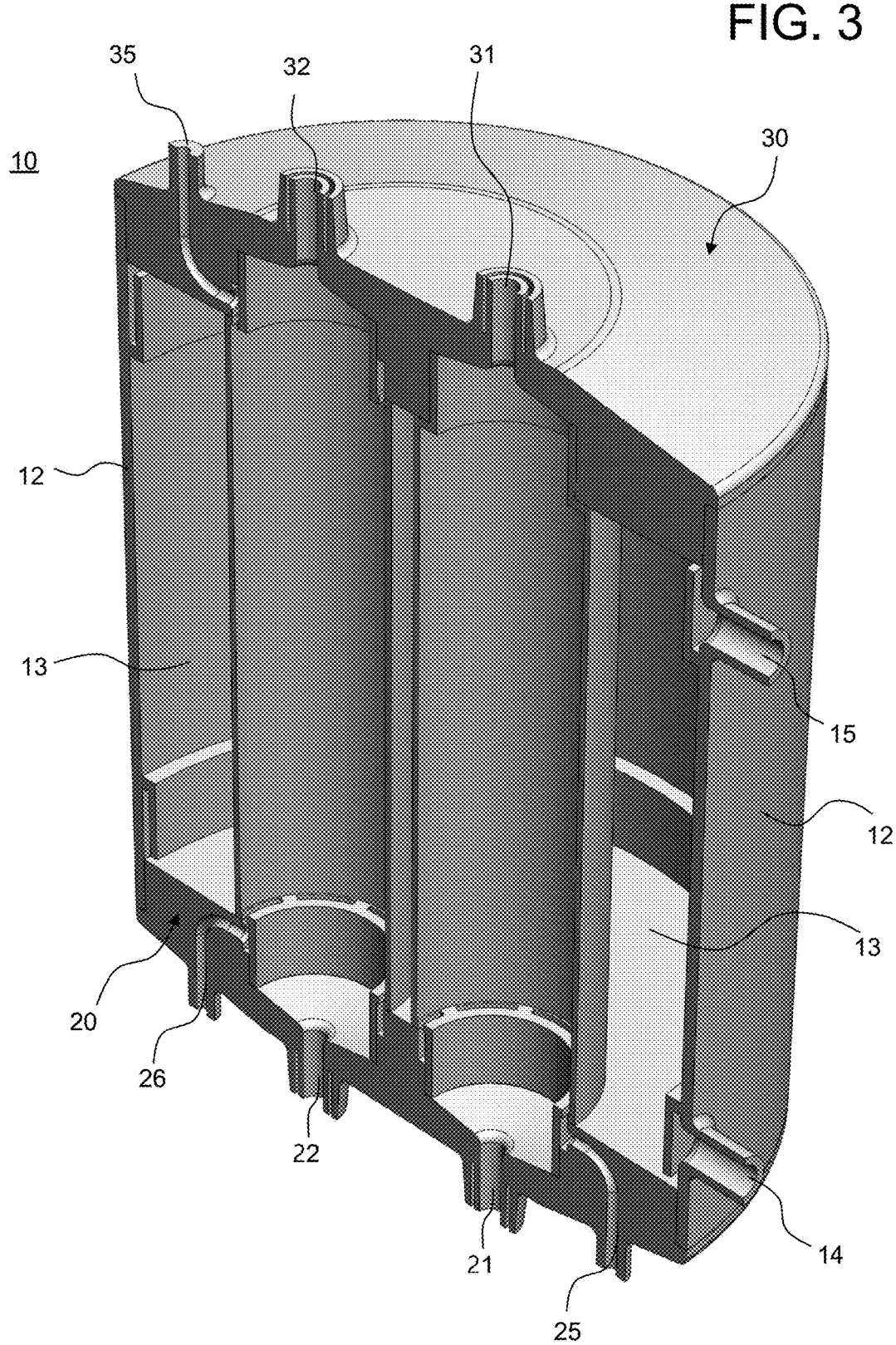

As shown in FIGS. 1 to 3, the blood purifying filter 10 may include a plasma separation filter 40, a hemodialysis filter 50, a housing, a plasma inlet port 14 and a plasma outlet port 15. The plasma separation filter 40 separates plasma from blood that is introduced from one side of the blood purifying filter 10. The hemodialysis filter 50 removes toxins and waste products from blood. The housing provides installation spaces for the plasma separation filter and the hemodialysis filter and defines a plasma flow section 13 outside the plasma separation filter and the hemodialysis filter. The plasma inlet port 14 is provided to allow plasma separated at the plasma separation filter 40 to flow into the plasma flow section 13. In contrast, the plasma outlet port 15 allows plasma having passed the plasma flow section 13 to be discharged out of the blood purifying filter 10. The housing includes a will 12 having a cylindrical shape, a lower cap 20 coupled to the plasma separation filter 40 and the hemodialysis filter 50 at a lower side of the wall 12, and an upper cap 30 coupled to the plasma separation filter 40 and the hemodialysis filter 50 at an upper side of the wall 12.

Figure 4:
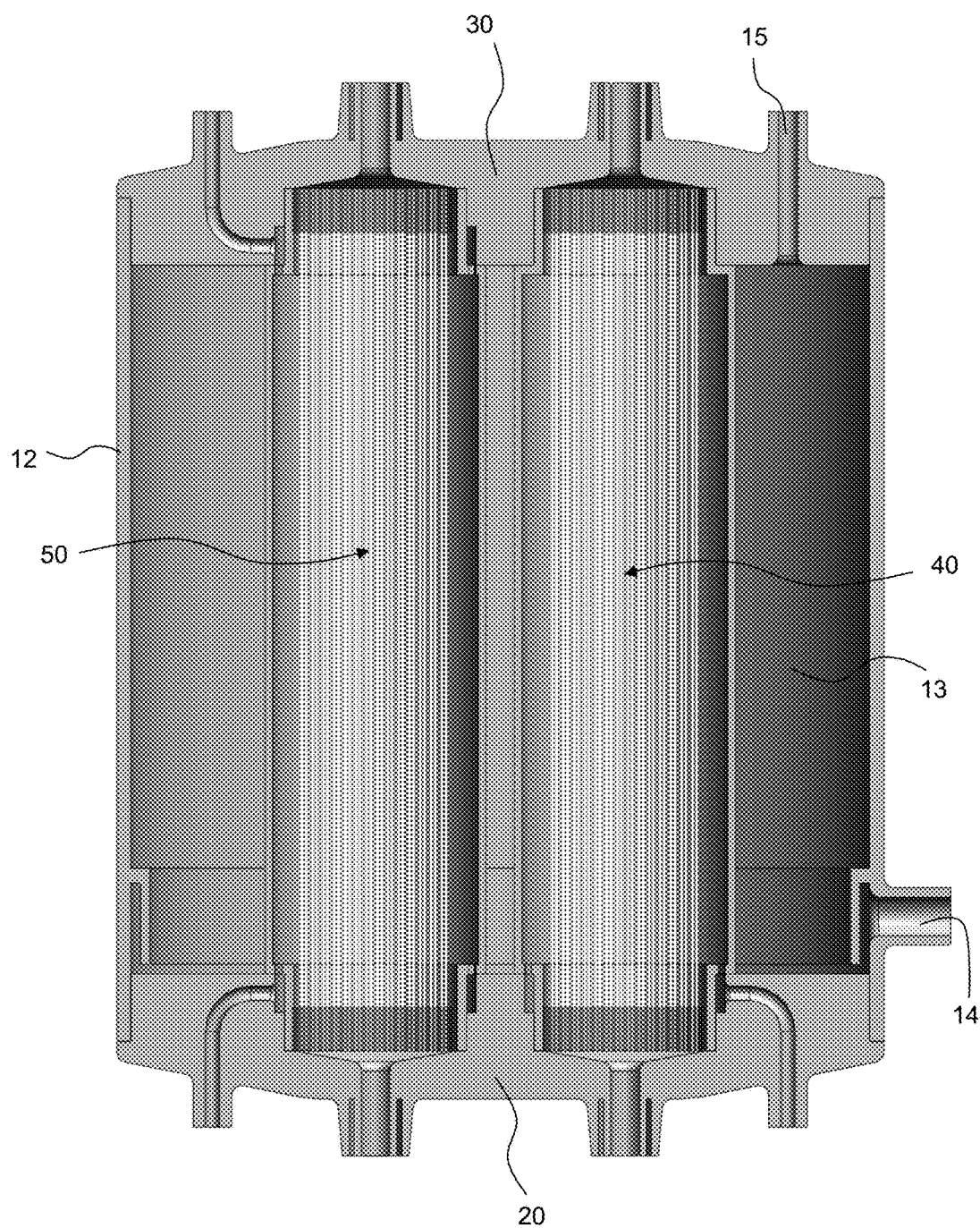
FIGS. 4 and 5 are cross-sectional views illustrating a blood purifying filter having plasma inlet and outlet ports disposed in a housing.
Figure 5:
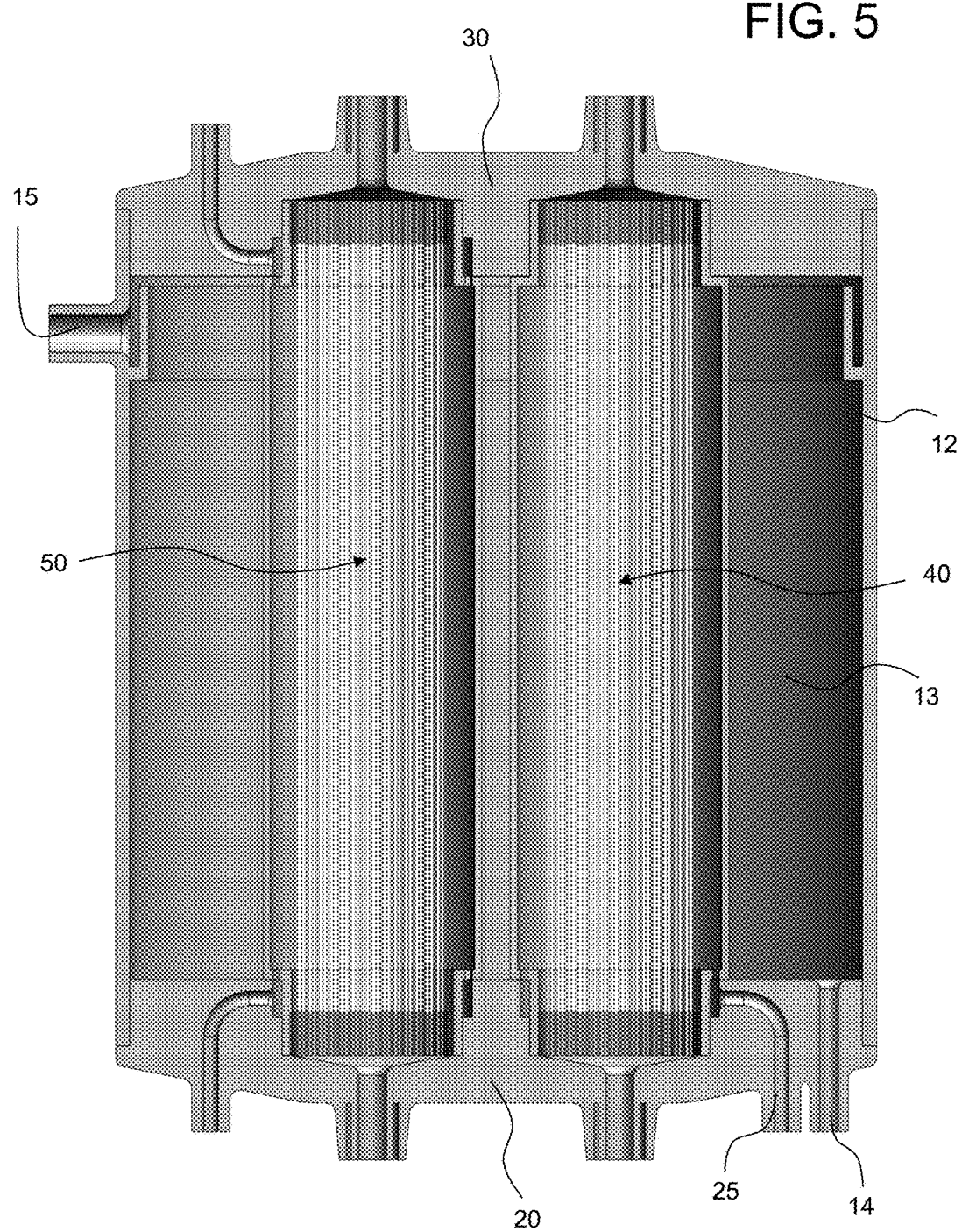

The plasma inlet and outlet ports 14 and 15 are disposed in the housing. As shown in FIGS. 1 to 3, the plasma inlet and outlet ports may be provided at the outer surface of the wall 12, and plasma introduced through the plasma inlet port 14 can be discharged out of the blood purifying filter 10 through the plasma outlet port 15 after passing through the plasma flow section 13. The plasma inlet and outlet ports 14 and 15 can also be disposed in the lower cap or in the upper cap, as illustrated in FIGS. 4 and 5. In this instance, one of the plasma inlet and outlet ports 14 and 15 is disposed in the lower cap 20 or on the wall 12 close to the lower cap and the other one may be disposed in the upper cap 30 or on the wall 12 close to the upper cap.

Figure 6:
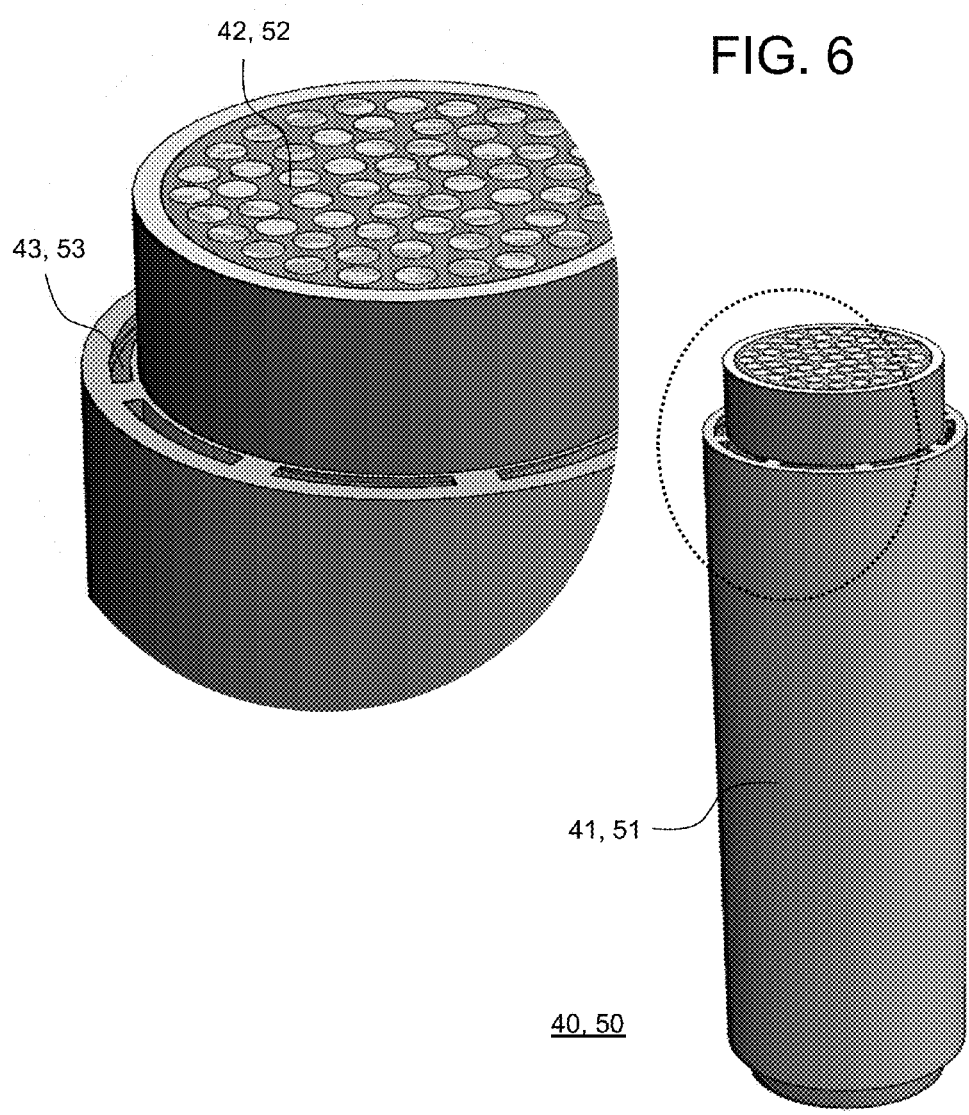
FIG. 6 is a perspective view of a plasma separation filter and a hemodialysis filter.

As shown in FIG. 6, the plasma separation filter 40 and the hemodialysis filter 50 may include a housing having an internal space thereof and a membrane disposed in the internal space of the housing. The internal space of the housing is divided by the membrane to allow two fluids to flow. In other words, the internal space of the plasma separation filter housing 41 is divided into a blood flow region and a plasma flow region by the plasma separation membrane 42, and the internal space of the hemodialysis filter housing 51 can be divided into a blood flow region and a dialysate flow region by the hemodialysis membrane 52.

FIG. 7 illustrates the lower cap 20 and the upper cap 30. The lower cap may be provided with a first lower-cap blood port 21 connected to the plasma separation filter 40, a second lower-cap blood port 22 connected to the hemodialysis filter 50, a first lower-cap insertion groove 23 to be easily coupled to the plasma separation filter 40, and a second lower-cap insertion groove 24 to be easily coupled to the hemodialysis filter 50. Likewise, the upper cap 30 may be provided with a first upper-cap blood port 31 connected to the plasma separation filter 40, a second upper-cap blood port 32 connected to the hemodialysis filter 50, a first upper-cap insertion groove 33 to be easily coupled to the plasma separation filter 40, and a second upper-cap insertion groove 34 to be easily coupled to the hemodialysis filter 50.

Both ends of the plasma separation filter 40 are coupled to the first lower-cap insertion groove 23 and the first upper-cap insertion groove 33 and both ends of the hemodialysis filter 50 are coupled to the second lower-cap insertion groove 24 and the second upper-cap insertion groove 34. When the plasma separation filter 40 and the hemodialysis filter 50 are coupled to the lower cap 20 and the upper cap 30, blood passing through the first lower-cap and the first upper-cap blood ports 21 and 31 flows into the blood flow region inside the plasma separation filter 40. Similarly, blood passing through the second lower-cap and the second upper-cap blood ports 22 and 32 flows into the blood flow region inside the hemodialysis filter 50.

In addition, as illustrated in FIG. 8, the plasma separation filter housing 41 may have a first flow hole 43 in a side thereof where the plasma separation filter housing 41 is coupled to the first lower-cap insertion groove 23. Also, the lower cap 20 may be additionally provided with a first lower-cap passage 25, which penetrates the lower cap 20, with one end thereof connected to the first lower-cap insertion groove 23. In this instance, the plasma separation filter 40 is coupled to the lower cap 20, allowing the first flow hole 43 provided in the plasma separation filter housing 41 and the first lower-cap passage 25 provided in the lower cap 20 to be connected to each other and thus forming a first flow path 61. Plasma of the plasma separation filter 40 flows through the first flow path 61.

In the same manner, as illustrated in FIG. 8, the hemodialysis filter housing 51 may have a second flow hole 53 in the side thereof where the hemodialysis filter housing 51 is coupled to the second lower-cap insertion groove 24, and the lower cap 20 may be additionally provided with a second lower-cap passage 26, which penetrates the lower cap, having one end connected to the second lower-cap insertion groove 24. When the hemodialysis filter 50 is coupled to the lower cap 20, the second flow hole 53 and the second lower-cap passage 26 are connected to each other, thus forming a second flow path 62. Dialysate can be supplied or discharged through the second flow path 62. When the blood purifying filter 10 has one flow path for dialysate, the supply of dialysate to the hemodialysis filter 50 and the discharge of the dialysate out of the hemodialysis filter may alternately occur.

However, the blood purifying filter 10 according to an embodiment of the present invention may have two separate dialysate flow paths in order to separate the inflow and outflow of dialysate. For this, as shown in FIG. 9, the hemodialysis filter housing 51 may further have a third flow hole 54 in a side where the hemodialysis filter housing 51 is coupled to the second upper-cap insertion groove 34, and the upper cap 30 may be provided with an upper-cap passage 35 which penetrates the upper cap 30 and is connected the second upper-cap insertion groove 34. When the hemodialysis filter 50 and the upper cap 30 are coupled to each other, a third flow path 63 connecting the third flow hole 54 and the upper-cap passage 35 may be formed. Dialysate can be supplied to the hemodialysis filter 50 through one of the second and third flow paths and then discharged through the other one.

Due to the coupling of the plasma separation filter 40 and hemodialysis filter 50 to the lower cap 20 and the upper cap 30, blood, plasma and dialysate are limited to flow into a predetermined region. Blood, plasma and dialysate are prevented from flowing to other spaces except predetermined spaces by chemical adhesion of each coupling part of the filters and caps or insertion of a soft O-ring such as silicone into each adhesion part.

Figure 10:
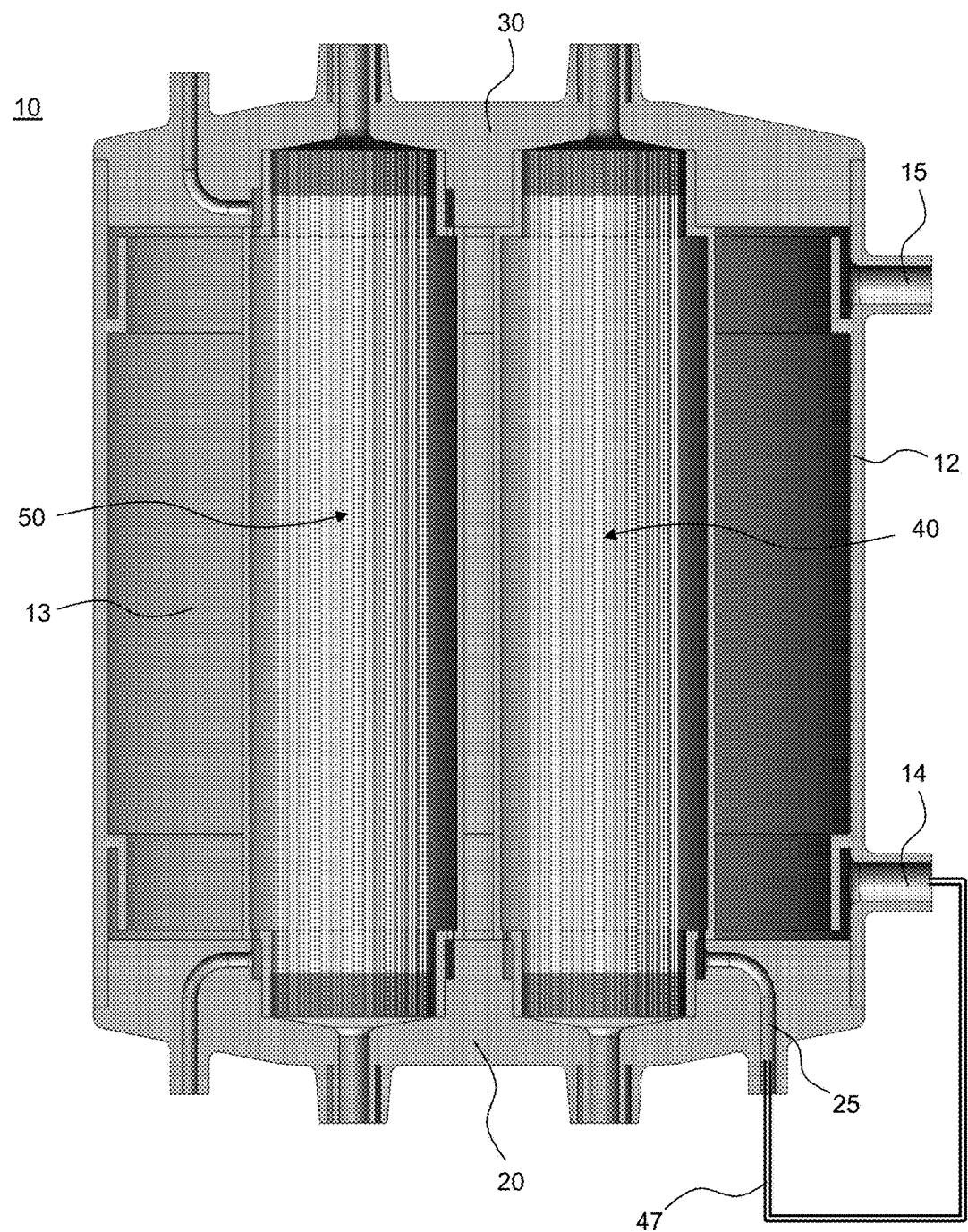
FIG. 10 is a cross-sectional view of a blood purifying filter having a plasma connection tube according to an embodiment of the present invention.

In addition, the blood purifying filter 10 according to an embodiment of the present invention may further include a plasma connection tube 47 which connects the lower cap 20 and the plasma inlet port 14. FIG. 10 illustrates the blood purifying filter 10 having the plasma connection tube 47. Plasma of the plasma separation filter 40 is discharged out of the plasma separation filter through the first lower-cap passage 25 and then supplied to the plasma flow section 13 through the plasma connection tube 47.

An adsorbent may be provided in the plasma flow section 13 to remove toxins and waste products from plasma. An anion exchange resin can remove electrically charged toxins such as bilirubin by means of ion exchange mechanism. On the other hand, activated charcoal removes tryptophan and water-soluble toxins of medium- to large-sized molecules by physical adsorption. The adsorbent may be used in a form of powder, particle, or block in which powder and particles are compressed. The adsorbent included in the blood purifying filter 10 according to an embodiment of the present invention is not limited in the type and number, and may be modified according to the purpose of the blood purifying treatment.

Here, when one of the plasma inlet and outlet ports 14 and 15 is provided in the lower cap 20 or on the wall 12 close to the lower cap 20, the other can be desirably provided in the upper cap 30 or on the wall 12 at a side to the upper cap 30, such that plasma introduced through the plasma inlet port 14 can sufficiently contact the adsorbent inside the plasma flow section 13.

Figure 11:
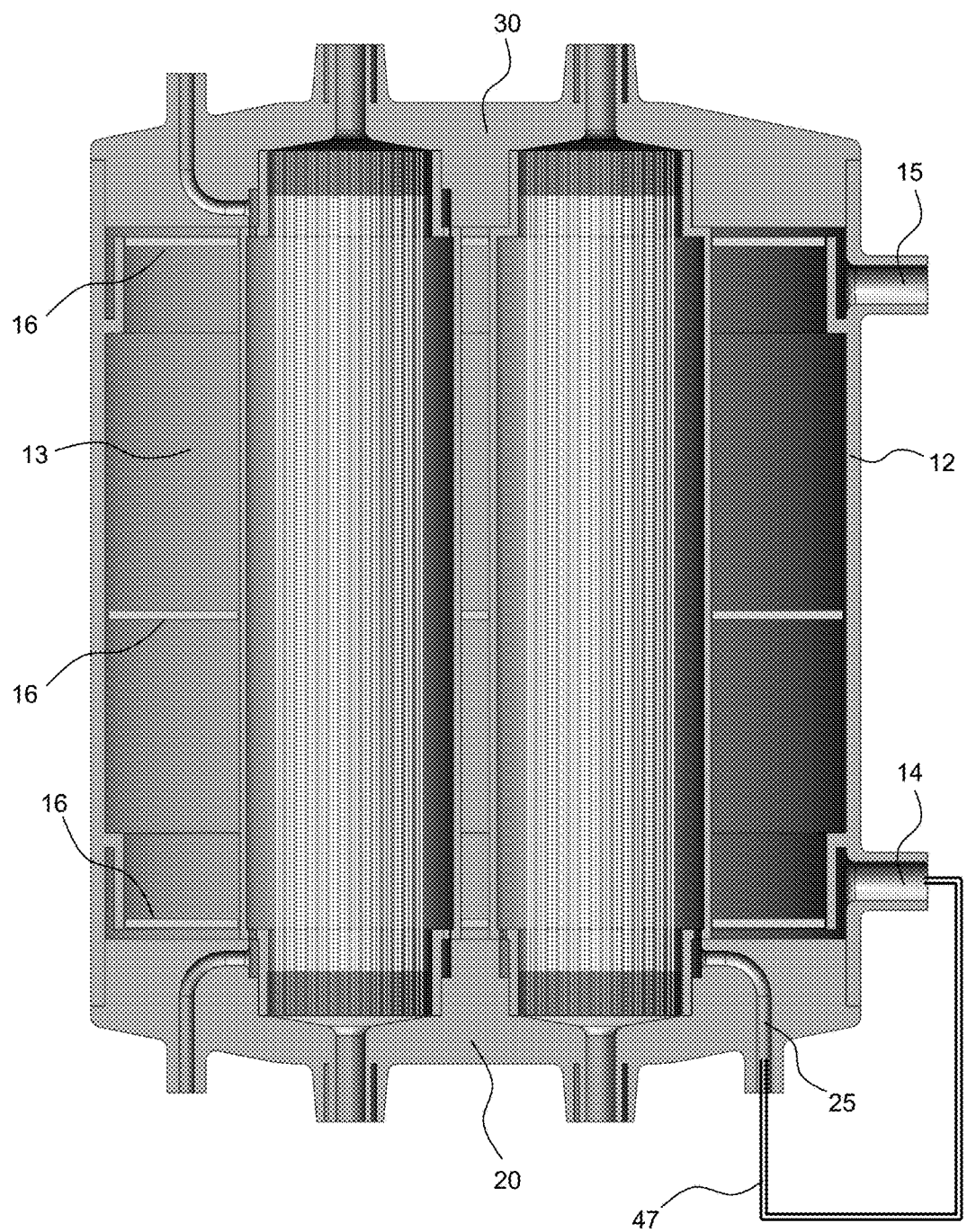
FIG. 11 is a cross-sectional view of a blood purifying filter having a separation wall.
Figure 12:
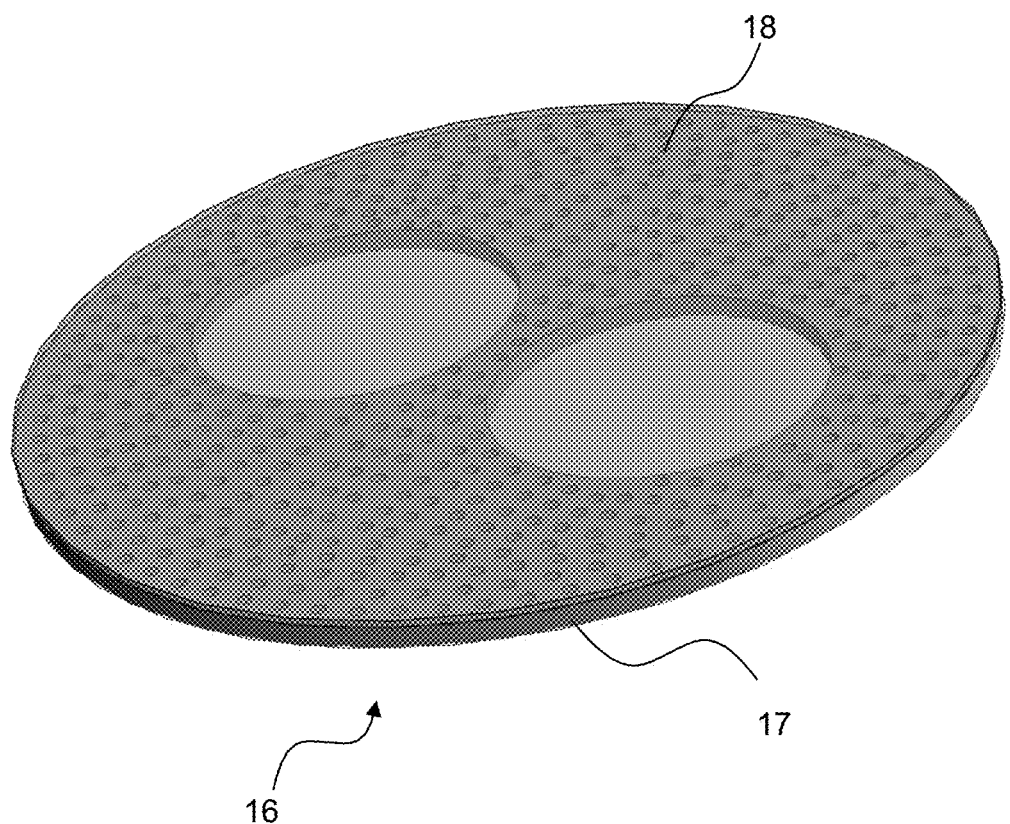
FIG. 12 is a perspective view of a separation wall.

The adsorbent must not move through the plasma inlet and outlet ports 14 and 15 and various methods can be used to prevent adsorbents from moving thorough the ports. For example, the plasma inlet and outlet ports 14 and 15 may be formed to have a size smaller than the adsorbent, or may be covered by a mesh filter with pores having a smaller size than the adsorbent. Also, the adsorbent may be covered by a mesh filter with pores having a smaller size than the adsorbent itself, or an adsorbent block in which powder or particles are compressed may be used. In addition, as illustrated in FIG. 11, a separation wall 16 may be disposed between the adsorbent and the plasma inlet port 14 or between the adsorbent and the plasma outlet port 15. The separation wall can be manufactured to have pores of a smaller size than the adsorbent, or may have a structure in which a mesh filter 18 having pores of a smaller size than the adsorbent is attached to a support wall 17, as shown in FIG. 12.

Similarly, when two or more kinds of adsorbent are used, the adsorbents may be covered by a mesh filter with pores of a smaller size than the adsorbents in order to prevent the adsorbents from mixing. Also, an adsorbent block in which powder or particles are compressed may be used, or the separation wall 16 may be disposed between the adsorbents.

Hereinafter, a blood purifying apparatus 70 according to an embodiment of the present invention will be described in detail with reference to the accompanying drawings.

Figure 13:
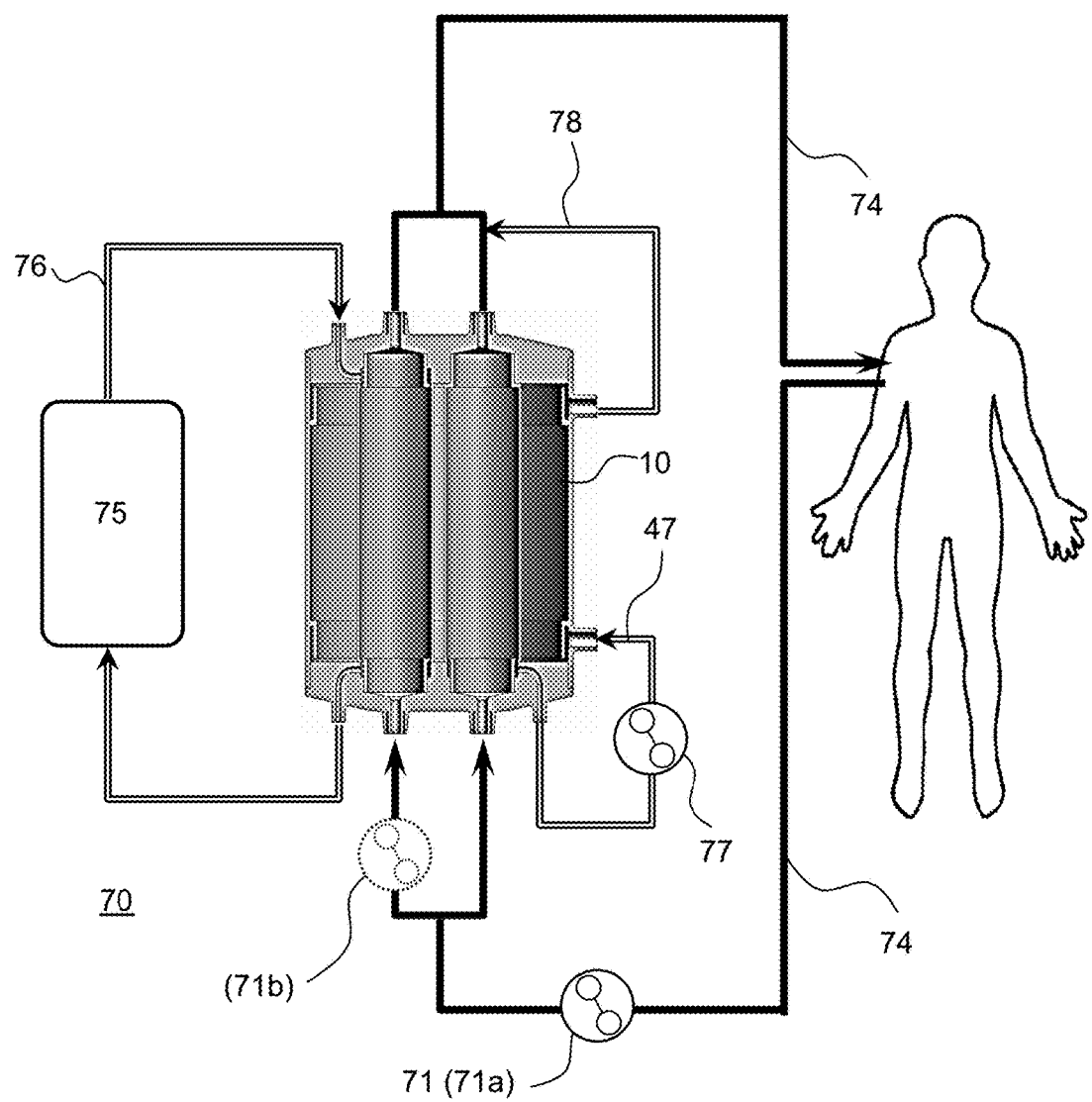
FIGS. 13 to 15 are views illustrating a blood purifying apparatus including a blood purifying filter according to an embodiment of the present invention.
Figure 14:
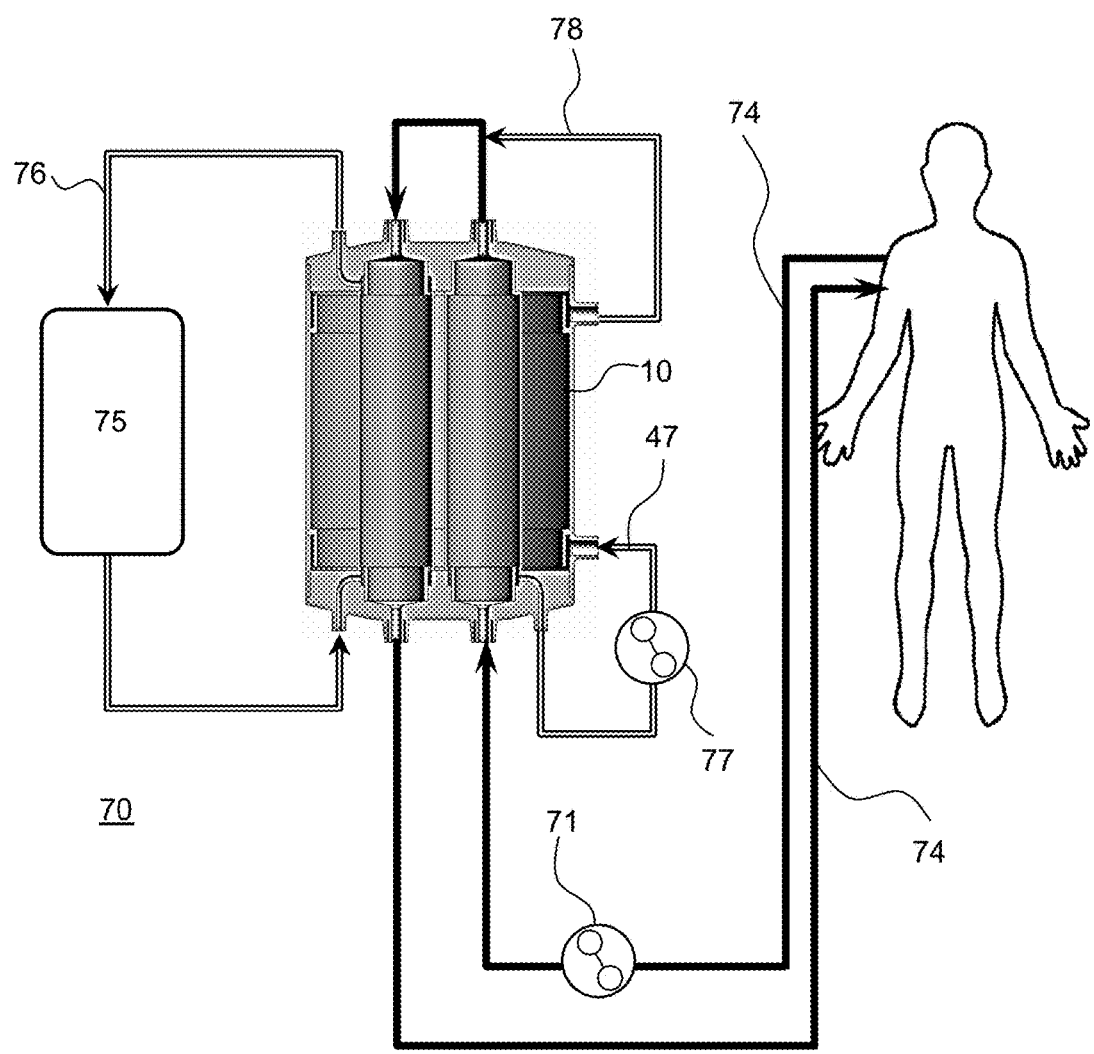
Figure 15:
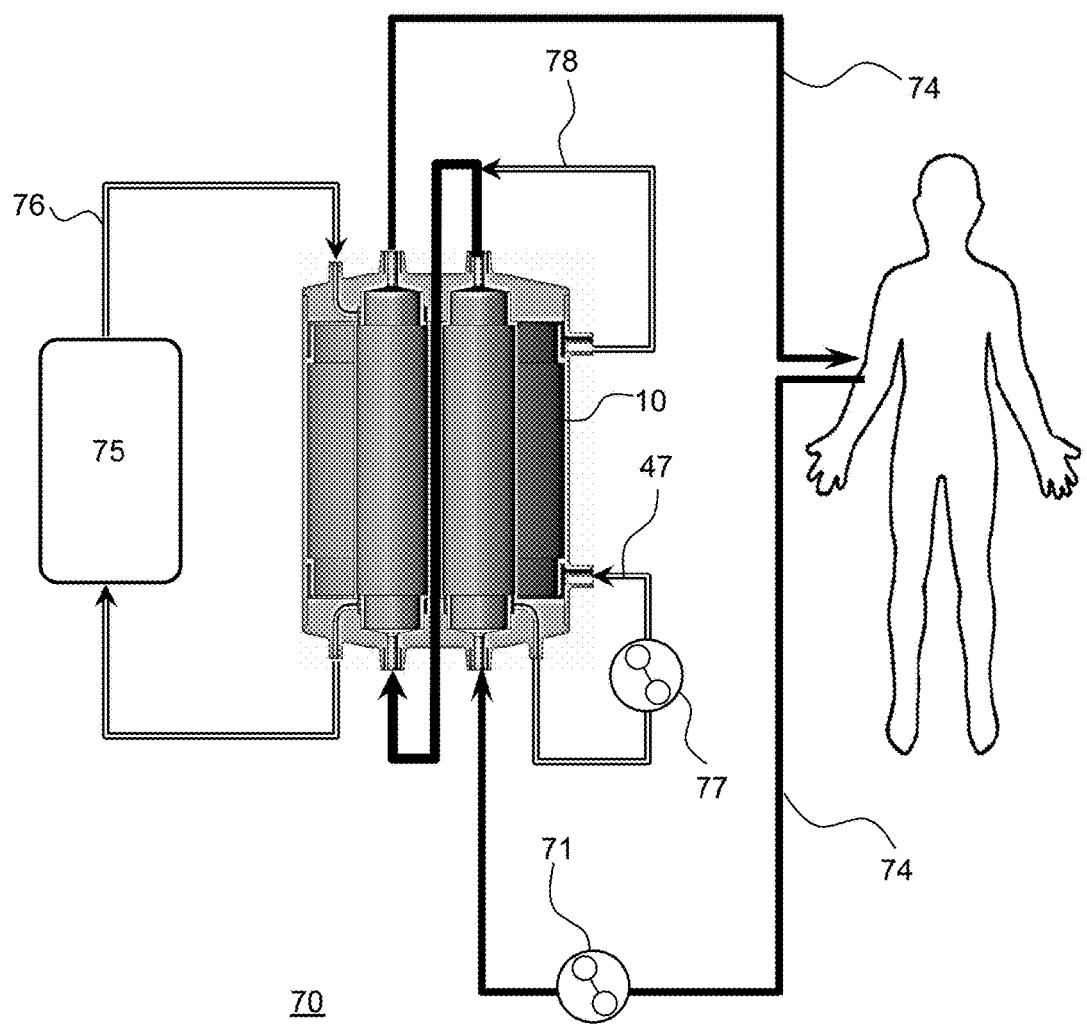
Figure 16:
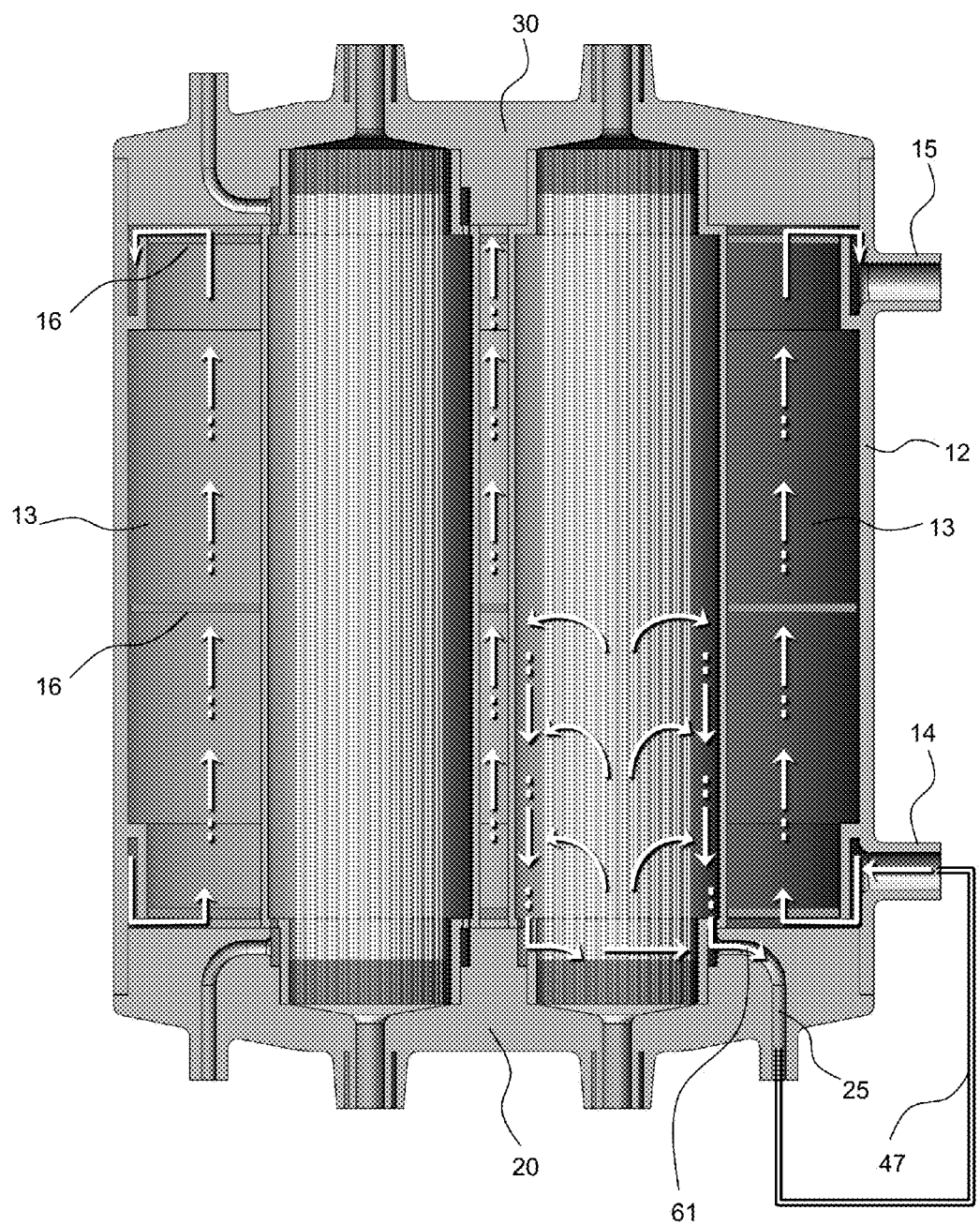
FIG. 16 is a cross-sectional view illustrating a flow of plasma inside a blood purifying filter.
Figure 17:
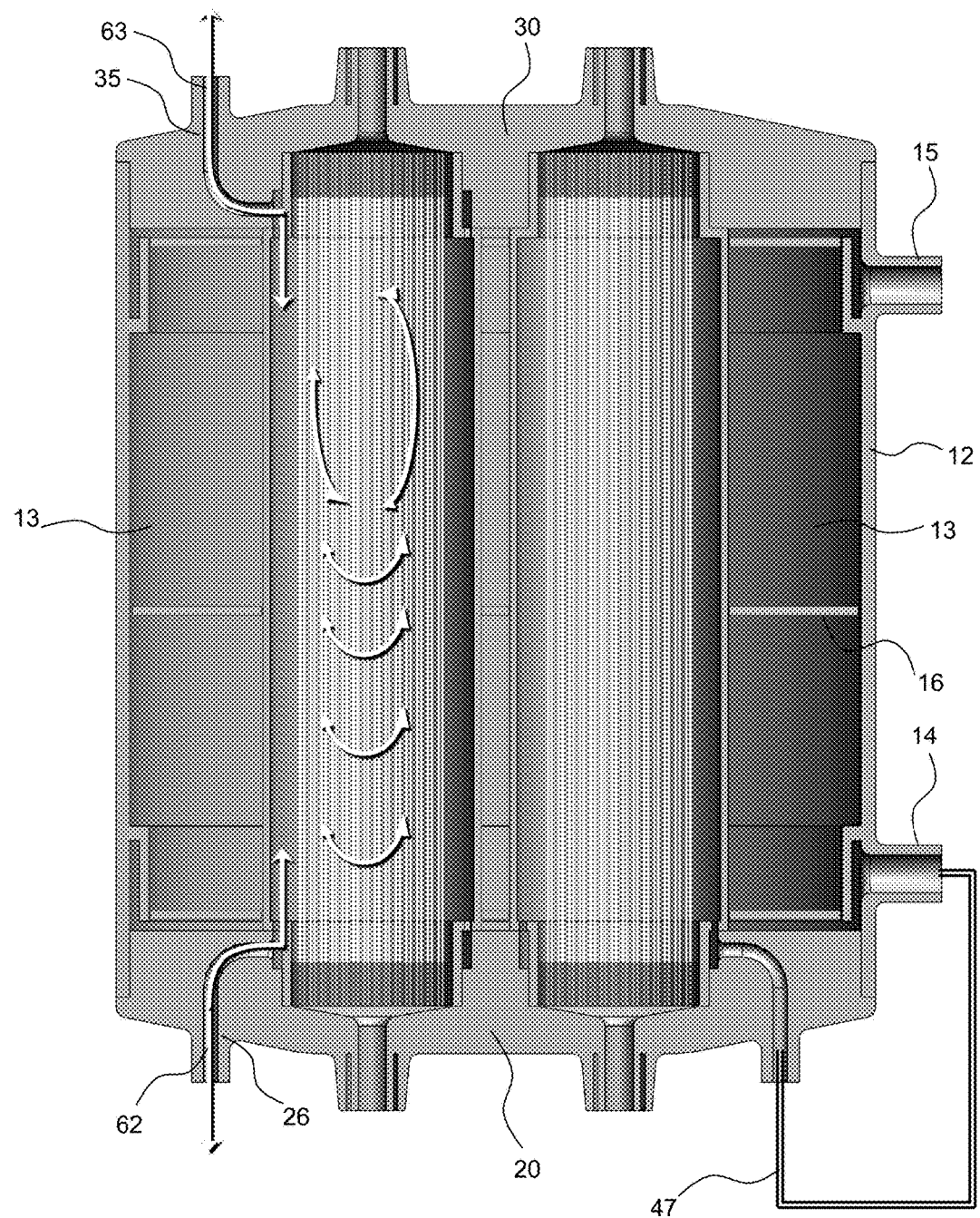
FIG. 17 is a cross-sectional view illustrating a flow of dialysate inside a blood purifying filter.

FIGS. 13 to 15 are views illustrating the blood purifying apparatus 70 including the blood purifying filter 10 according to an embodiment of the present invention. FIGS. 16 and 17 are cross-sectional views illustrating the flow of plasma and dialysate inside the blood purifying filter 10, respectively.

As shown in FIGS. 13 to 15, the blood purifying apparatus 70 may include the blood purifying filter 10, a blood flow tube 74 connecting a patient and the blood purifying filter 10 and allowing blood to flow therein, a blood pump 71 disposed on the blood flow tube to transfer blood, a plasma pump 77 disposed on the plasma connection tube 47 to transfer plasma, a plasma flow tube 78 connecting the plasma outlet port 15 and the blood flow tube 74 to allow plasma to flow therein, and a dialysate supply device 75 supplying dialysate into the hemodialysis filter 50 and collecting dialysate or filtrate from the hemodialysis filter. An additional plasma pump 77 may be provided on the plasma flow tube 78.

As illustrated in FIGS. 13 to 15, the blood purifying apparatus 70 according to an embodiment of the present invention may have different configurations of blood flow. The arrows in the drawings indicate the flow direction of blood, plasma and dialysate. First, FIG. 13 illustrates the blood purifying apparatus 70 having a structure in which blood is divided separated into the plasma separation filter 40 and the hemodialysis filter 50. Blood of a patient is divided into the first and second lower-cap blood ports 21 and 22, allowing plasma separation and hemodialysis to occur simultaneously, and then returned to a patient through the first and second upper-cap blood ports 31 and 32. In this case, the blood pump 71 can be separated into a plasma separation blood pump 71$a$ and a hemodialysis blood pump 71$b$ to regulate the blood flow rate flowing into the plasma separation filter 40 and the hemodialysis filter 50.

On the other hand, as shown FIGS. 14 and 15, blood may also flow through the plasma separation filter 40 and the hemodialysis filter 50 in consecutive order. In FIG. 14, blood is introduced to the plasma separation filter 40 through the first lower-cap blood port 21 and plasma is separated from the blood therein-Residual blood including blood cells passes through the first upper-cap blood port 31 and then the second upper-cap blood port 32 to flow into the hemodialysis filter 50. That is, the blood flow in FIG. 14 has a structure of "patient→first lower-cap blood port→plasma separation filter→first upper-cap blood port→second upper-cap blood port→hemodialysis filter→second lower-cap blood port-→patient". In contrast, the blood flow in FIG. 15 has a structure of "patient→first lower-cap blood port→plasma separation filter→first upper-cap blood port→second lower-cap blood port→hemodialysis filter→second upper-cap blood port→patient".

In the blood purifying apparatus 70 in which blood passes the plasma separation filter 40 and the hemodialysis filter 50 sequentially shown in FIGS. 14 and 15, plasma having passed through the plasma flow section 13 can be returned to the blood flow tube 74 connecting between the outlet of the plasma separation filter 40 and the inlet of the hemodialysis filter 50. In this instance, the hematocrit % of blood entering into the hemodialysis filter 50 can be lowered due to the mix of plasma with blood, which further reduces the risk of coagulation. In addition, the blood flow rate passing through the plasma separation filter 40 and the hemodialysis filter 50 can be maintained at a rate enough for the treatment despite the use of a single blood pump 71.

The blood flow of the blood purifying apparatus 70 according to an embodiment of the present invention is not limited to the structures shown in the drawings, but may be modified into other structures. For example, blood may pass the hemodialysis filter 50 first and then the plasma separation filter 40 before it is returned to a patient. In other words, the blood flow can be modified in various structures to increase the blood flow stability and attain blood flow rates required for the treatment. In this regard, the blood flow flowing through the plasma separation filter 40 and the hemodialysis filter 50 can be configured in parallel to each other or in an opposite direction.

The blood pump 71 operates and blood of a patient flows into the plasma separation filter 40. Due to fluid pulling by the plasma pump 77 disposed on the plasma connection tube 47, the hydraulic pressure of the plasma flow region inside the plasma separation filter 40 is lowered below the pressure in the blood flow region, and plasma can be separated across the plasma separation membrane 42. The separated plasma moves to the plasma flow section 13 through the plasma connection tube 47. FIG. 16 illustrates the flow of plasma inside the blood purifying filter 10. Plasma having passed through the adsorbent is returned to the blood flow tube 74. When there are a plurality of plasma inlet and outlet ports 14 and 15, a plurality of plasma pumps 77 may be provided to control the plasma flow rates through each of the plasma inlet and outlet ports.

Also, dialysate is supplied to the hemodialysis filter 50 or discharged from the hemodialysis filter by the operation of the dialysate supply device 75. If dialysate is supplied through one of the second and third flow paths 62 and 63, dialysate can be discharged through the other port. However, blood and dialysate are desired to flow in an opposite direction inside the hemodialysis filter 50. In addition, the hemodialysis filter 50 can be easily switched into a function of hemofiltration in which excess water and waste products in blood are removed by the fluid pulling due to the dialysate supply device 75 without the supply and discharge of dialysate by the dialysate supply device 75.

Particularly, in the blood purifying apparatus 70 according to an embodiment of the present invention, the hydraulic pressure of plasma flowing into the plasma flow section 13 may be positive (+) value which is higher than the atmosphere pressure. In case that the plasma connection tube 47 is not provided, plasma flow can be achieved by the operation of the plasma pump 77 provided in the plasma flow tube 78 connecting the plasma outlet port 15 and the blood flow tube 74. In this case, plasma needs to pass the plasma separation membrane 42, a plasma passage connecting the plasma separation filter 40 and the plasma flow section 13, and adsorbents in the plasma flow section. Despite the fluid pulling by the plasma pump, a flow resistance to the plasma flow is largely created, giving rise to the lower pressure in the plasma separation filter 40 and the plasma flow section 13 than atmosphere pressure. Negative pressures inside the blood purifying apparatus not only increase the risk of air inflow to the apparatus, but the plasma flow rates and toxin removals are also substantially restricted.

However, the blood purifying filter 10 according to an embodiment of the present invention is provided with the first flow path 61 connecting the first flow hole 43 and the first lower-cap passage 25 and the plasma connection tube 47 connecting the first flow path 61 and the plasma inlet port 14. Accordingly, plasma passing through the plasma connection tube 47 and the plasma flow section 13 can be transferred due to the fluid pushing by the plasma pump, instead of fluid pulling, disposed on the plasma connection tube 47, such that the pressure of plasma flowing into the plasma flow section 13 can be maintained positive (+) values. Positive plasma pressures can further prevent such problems as an air inflow or the reduction in the plasma flow rate and toxin removal.

Thus, the blood purifying filter 10 according to the embodiments of the present invention can efficiently purify blood of a patient, by optimizing the plasma flow inside the filter and integrating a plasma separation process for separating plasma from blood, an adsorption process for removing hepatic toxins or protein-bound toxins from the separated plasma, and a hemodialysis process for removing uremic toxins and water-soluble toxins from blood. In addition, the blood purifying apparatus 70 having the blood purifying filter 10 can further provide the convenience in installation and use, and the reduction in the treatment cost by using one filter.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A blood purifying filter comprising:
a plasma separation filter separating plasma from blood;
a hemodialysis filter disposed in parallel with the plasma separation filter and removing toxins and waste products from blood;
a housing providing installation space for the plasma separation filter and the hemodialysis filter and defining a plasma flow section outside the plasma separation filter and the hemodialysis filter;
a plasma inlet port provided in the housing to allow separated plasma to flow into the plasma flow section; and
a plasma outlet port provided in the housing to allow plasma having passed the plasma flow section to be discharged out of the blood purifying filter, wherein the housing comprises a wall having a cylindrical shape, a lower cap coupled to the plasma separation filter and the hemodialysis filter at a lower side of the wall, and an upper cap coupled to the plasma separation filter and the hemodialysis filter at an upper side of the wall, wherein the plasma separation filter comprises a plasma separation filter housing having an internal space and a membrane accommodated in the internal space of the plasma separation filter housing and the hemodialysis filter comprises a hemodialysis filter housing having an internal space and a membrane accommodated in the internal space of the hemodialysis filter housing, wherein a plasma connection tube is further provided to connect the plasma inlet port and the lower cap.

2. The blood purifying filter of claim 1, wherein:
the lower cap comprises a blood port through which blood passes, a lower-cap insertion groove coupled to the plasma separation filter and the hemodialysis filter, and a lower-cap passage which penetrates the lower cap, wherein one end of the lower-cap passage is connected to the lower-cap insertion groove; and
the upper cap comprises a blood port through which blood passes, an upper-cap insertion groove coupled to the plasma separation filter and the hemodialysis filter, and an upper-cap passage which penetrates the upper cap, wherein one end of the upper-cap passage is connected to the upper-cap insertion groove.

3. The blood purifying filter of claim 2, wherein
the plasma separation filter housing has a flow hole at a side where the plasma separation filter housing is coupled to the lower-cap insertion groove or the upper-cap insertion groove to allow plasma to pass therethrough.

4. The blood purifying filter of claim 3, wherein the hemodialysis filter housing has a flow hole at a side where the hemodialysis filter housing is coupled to the lower-cap insertion groove or the upper-cap insertion groove to allow dialysate to pass therethrough.

5. The blood purifying filter of claim 4, wherein the flow hole is formed to surround the plasma separation filter housing or the hemodialysis filter housing.

6. The blood purifying filter of claim 4, comprising an adsorbent in the plasma flow section to remove toxins and waster products from plasma.

7. The blood purifying filter of claim 6, wherein when one of the plasma inlet port and the plasma outlet port is provided in the lower cap or on the wall close to the lower cap, the other one is provided in the upper cap or on the wall close to the upper cap.

8. The blood purifying filter of claim 7, wherein in order to prevent the adsorbent from moving through the plasma inlet and outlet ports:
the plasma inlet and outlet ports are formed to have a size smaller than the adsorbent;
the plasma inlet and outlet ports are covered by a mesh filter with pores having a smaller size than the adsorbent;
the adsorbent is covered by a mesh filter with pores having a smaller size than the adsorbent;
an adsorbent block in which powder or particles are compressed is used; or
a separation wall is disposed between the adsorbent and the plasma inlet port or between the adsorbent and the plasma outlet port to inhibit passing of the adsorbent.

9. The blood purifying filter of claim 8, wherein:
the separation wall is manufactured to have pores of a smaller size than the adsorbent or has a structure in which a mesh filter having pores of a smaller size than the adsorbent is attached to a support wall.

10. A blood purifying apparatus comprising:
a blood purifying filter according to claim 6;
a blood flow tube connecting between the blood purifying filter and a patient and allowing blood to flow therein;
a blood pump disposed on the blood flow tube to transfer blood;
a plasma pump disposed on the plasma connection tube to transfer plasma;
a plasma flow tube connecting between the plasma outlet port and the blood flow tube to allow plasma to flow therein; and
a dialysate supply device supplying dialysate into the hemodialysis filter or collecting dialysate or filtrate from the hemodialysis filter.

11. A blood purifying apparatus of claim 10, further comprising a plasma pump disposed on the plasma flow tube.

12. A blood purifying apparatus of claim 11, wherein in order to prevent the adsorbent from moving through the plasma inlet and outlet ports:
the plasma inlet and outlet ports are formed to have a size smaller than the adsorbent;
the plasma inlet and outlet ports are covered by a mesh filter with pores having a smaller size than the adsorbent;
the adsorbent is covered by a mesh filter with pores having a smaller size than the adsorbent;
an adsorbent block in which powder or particles are compressed is used; or
a separation wall is disposed between the adsorbent and the plasma inlet port or between the adsorbent and the plasma outlet port to inhibit passing of the adsorbent.

13. A blood purifying apparatus of claim 12, wherein:
the separation wall is manufactured to have pores of a smaller size than the adsorbent or has a structure in which a mesh filter having pores of a smaller size than the adsorbent is attached to a support wall.

* * * * *